(12) United States Patent
Zavarzin et al.

(10) Patent No.: US 8,293,207 B2
(45) Date of Patent: Oct. 23, 2012

(54) RADIOMETAL-LABELED AMINO ACID ANALOGS, IMAGING AND THERAPEUTIC AGENTS INCORPORATING THE SAME, AND METHODS USING THE SAME

(76) Inventors: Valery Zavarzin, Newton, MA (US); Irving Weinberg, Besthesda, MD (US)

( * ) Notice: Subject to any disclaimer, the term of this patent is extended or adjusted under 35 U.S.C. 154(b) by 419 days.

(21) Appl. No.: 12/562,788

(22) Filed: Sep. 18, 2009

(65) Prior Publication Data
US 2011/0070157 A1    Mar. 24, 2011

(51) Int. Cl.
*A61K 51/00*    (2006.01)
*A61M 36/14*    (2006.01)

(52) U.S. Cl. .................... 424/1.69; 424/1.11; 424/1.65; 424/1.81; 424/9.1; 206/570

(58) Field of Classification Search ............... 424/1.11, 424/1.65, 1.69, 9.1, 1.81; 514/1, 1.1; 530/300; 206/223, 569, 570
See application file for complete search history.

(56) References Cited

U.S. PATENT DOCUMENTS
5,808,146 A    9/1998  Goodman et al.
2007/0082879 A1  4/2007  Goodman

*Primary Examiner* — D L Jones
(74) *Attorney, Agent, or Firm* — Barnes & Thornburg LLP

(57) ABSTRACT

An amino acid analog is provided, in syn-stereoisomeric form, anti-stereoisomeric form, or a combination thereof. The amino acid analog includes a cyclobutane ring with at least one of an amine group and a carboxyl group attached to one carbon node of the cyclobutane ring. A chain of moieties X, Y, and Z attached to one of remaining three carbon nodes of the cyclobutane ring. X is a chelating agent selected from a group comprising DCTA, DOTA, DTPA, EDTA, NOTA, PCTA, and TETA. Y is a linking moiety selected from a group comprising —NH—CO— and —NH-p-CHSN-Bn- where the linking moiety facilitates incorporation of the chelating agent into the amino acid analog. Z is a metal radioisotope selected from a group comprising Cu-60, Cu-61, Cu-62, Cu-64, Cu-67, Ga-67, Ga-68, Y-86, Y-88, Y-90, Sr-85, Sr-89, Gd-153, Gd-157, Sm-153, Lu-177, W-185, Re-186, Re-188, and Ir-192.

8 Claims, 1 Drawing Sheet

RADIOMETAL-LABELED AMINO ACID ANALOGS, IMAGING AND THERAPEUTIC AGENTS INCORPORATING THE SAME, AND METHODS USING THE SAME

CROSS-REFERENCE TO RELATED APPLICATION(S)

This U.S. patent application is a first-filed patent application and does not rely on any other patent application for priority.

FIELD OF THE INVENTION

The present invention concerns the structure of selected amino acids that incorporate radioactive tracers that may be injected in a patient to assist with and enhance radio-diagnostic and radio-therapy procedures. Radio-diagnostic procedures include, but not limited to, photon emission tomography ("PET") and single photon emission computed tomography ("SPECT") techniques. More specifically, the present invention concerns the structure of a class of novel amino acid compounds that are useful in detection, staging, and therapy of prostate cancers and other body tumors, as examples.

SUMMARY OF THE INVENTION

Radio-diagnostic and radio-therapy techniques typically rely on peptides, sugars, and other biologically-active compounds that incorporate radioactive materials with a relatively short half-life.

Typically, medical practitioners prepare artificial amino acid analogs for radio-therapy that exhibit certain metabolic properties of natural amino acids. The amino-acids are "artificial" in that similar molecular structures do not occur in animals or humans.

Reference is made to U.S. Pat. No. 5,808,146 and U.S. Patent Application Publication No. 2007/0082879, which describe the beneficial properties of certain fluorine-18-based, artificial amino acid for medical imaging that have been studied.

By way of further example, reference is made to products offered by Macrocyclics, a company in Dallas, Tex. Products offered by this company provide some examples of biologically-active materials that may be employed in radio-diagnosis and radio-therapy. At this company's website, bi-functional chelating agents are described that enable synthesis of complex biological metal-chelating compounds with high yield, stability, and purity.

Currently, there are two radioisotopes that are preferred the preferred choice for imaging in nuclear medicine: (1) Tc-99m (which is useful for SPECT) and (2) F-18 (which is useful for PET).

As should be appreciated by those skilled in the art, PET provides better spatial resolution and quantization. However, because of the short half-life of F-18 (approximately two hours), there is a requirement that the cyclotron facility be physically close to the medical clinic.

This presents a challenge for those medical facilities that do not have convenient access to a cylclotron.

SUMMARY OF THE INVENTION

It is therefore, one aspect of the present invention to provide a class of novel amino acid compounds that do not require access to cyclotron for manufacture.

Specifically, the present invention provides for a class of novel amino acid compounds that that are useful in detection, staging and therapy of prostate and other body tumors.

These compounds may be conveniently labeled with multiple metal radioisotopes such as Cu-60, Cu-61, Cu-62, Cu-64, Cu-67, Ga-67, Ga-68, Y-86, Y-88, Y-90, Sr-85, Sr-89, Gd-153, Gd-157, Sm-153, Lu-177, W-185, Re-186, Re-188, and Ir-192, some of which are suitable for PET and SPECT imaging techniques and radioisotope therapy.

The present invention contemplates that some of the suitable radioisotopes can be obtained from an on-site, low-cost isotope generator, such as a Zn-62/Cu-62 or a Ge-68/Ga-68 isotope generator known to those skilled in the art.

It is one aspect of the present invention to provide an amino acid analog in at least one of syn-stereoisomeric form, anti-stereoisomeric form, or a combination thereof. The amino acid analog includes a cyclobutane ring with at least one of an amine group and a carboxyl group attached to one carbon node of the cyclobutane ring. A chain of moieties X, Y, and Z attached to one of remaining three carbon nodes of the cyclobutane ring. X is a chelating agent selected from DCTA, DOTA, DTPA, EDTA, NOTA, PCTA, TETA, TE2A, and DO2A. Y is a linking moiety selected from a group comprising —NH—CO— and —NH-p-CHSN-Bn- where the linking moiety facilitates incorporation of the chelating agent into the amino acid analog. Z is a metal radioisotope selected from a group comprising Cu-60, Cu-61, Cu-62, Cu-64, Cu-67, Ga-67, Ga-68, Y-86, Y-88, Y-90, Sr-85, Sr-89, Gd-153, Gd-157, Sm-153, Lu-177, W-185, Re-186, Re-188, and Ir-192.

In another aspect of the amino acid analog of the present invention, at least one moiety R is added, with the moiety R being selected from a group of isomeric forms of $CH_3$, $C_2H_5$, $C_3H_8$, $C_4H_{10}$. The moiety is attached to one of the remaining two carbon nodes on the cyclobutane ring.

In one specific embodiment, the amino acid analog of the present invention incorporates DOTA as the chelating agent and —NH-p-CHSN-Bn- as the linking group.

In still another specific embodiment, the amino acid analog of the present invention incorporates NOTA as the chelating agent X and —NH-p-CHSN-Bn- as the linking group Y.

It is contemplated that the amino acid analog of the present invention may incorporate Ga-68 produced by a Ge/Ga isotope generator for the radioisotope Z.

Additionally, the amino acid analog of the present invention may include Cu-62 produced by a Zn/Cu isotope generator for the radioisotope Z.

The amino acid analog alternatively may rely on a radioisotope Z provided from an automated microprocessor-controlled Ge/Ga generator and purification system with an injectable radiopharmaceutical preparation operation integrated therein. The importance of this aspect lies in the notion that, given a sixty-eight (68) min. decay time of Ga-68 isotope and its relatively slow reaction with clinically acceptable chelators, only an automated system is likely to produce radiopharmaceuticals with reliably reproducible qualities satisfying USP and FDA guidelines.

For the amino acid analog of the present invention, it is contemplated that the linking group Y may be a residue of reaction from an isothiocyanate arm of a bi-functional chelator with an amine residue.

The present invention also contemplates a method of synthesizing an amino acid analog. The method includes the steps of preparing a precursor compound with a —NH$_2$ moiety in place of an -Y-X-Z moiety, reacting the precursor with a bi-functional chelating agent selected from a group including p-SCN-Bn-DOTA and p-SCN-Bn-NOTA to produce reaction products, HPLC-separating the reaction products, and purifying the reaction products.

The method contemplated by the present invention may be such that the bi-functional chelating agent is reacted with the precursor in a dimethyl sulfoxide media.

The present invention also contemplates a diagnostic composition for tumor imaging that combines the amino acid analog described herein with a suitable carrier.

A kit for production of a radiopharmaceutical is a further aspect of the present invention. The kit includes a septum closed vial containing at least one of a lyophilized or freeze-dried amino acid analog as described herein. The kit also includes an excipient and at least one compound providing pH adjustment to the range 5.0-7.8 and additionally provides adjustment to physiological isotonicity for injection when admixed with a volume of sterile water. At least one compound reconstitutes the vial contents by bringing the vial contents into solution.

The present invention also contemplates a method of tumor imaging by at least one of positron emission tomography or single photon emission tomography. The method includes the steps of (a) administering to a subject, a tumor-revealing amount of the an amino acid analog as described herein, (b) allowing sufficient time for biodistribution in the subject, and (c) measuring the distribution of the compound by means of PET or SPECT.

In addition, the present invention contemplates a method of tumor radiotherapy involving administering to a subject having a tumor, a tumor-curing amount of the amino acid analog described herein.

Other aspects of the present invention should be apparent to those skilled in the art after considering the scope and content of the instant disclosure.

BRIEF DESCRIPTION OF THE DRAWINGS

The present invention will now be described in connection with the following drawings, in which.

DETAILED DESCRIPTION OF
EMBODIMENT(S) OF THE INVENTION

The present invention will now be described in connection with one or more examples. It is intended for the discussion of specific examples to be merely exemplary of the broad scope of the present invention. In other words, as should be appreciated by those skilled in the art, the invention is not intended to be limited solely to the examples described herein. To the contrary, the present invention encompasses any equivalents and variations that may be appreciated by those skilled in the art.

The present invention is directed to several aspects associated with a group of amino acid analogs that have been modified to include several specific features.

Figure 1A:
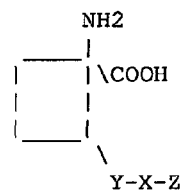
FIGS. 1A and 1B are illustrations of two novel radiotracer molecules, which are represented as combinations of the following: a cyclobutane ring, a linking group Y, a strong chelating agent X, and a metallic radioisotope Z, where the square represents the cyclobutane ring C$_4$H$_8$.
Figure 1B:
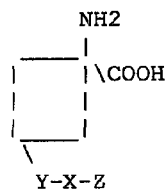

FIGS. 1A and 1B illustrate two embodiments of the amino acid analog of the present invention. As illustrated, the amino acid analog molecule consists of a combination of the following: (1) a cyclobutane ring to which is attached (2) a strong chelating agent X (by means of a linking group Y), and (3) a metallic radioisotope Z. The square in the figures represents the cyclobutane ring C$_3$H$_8$.

The linking group Y may be selected from any of a number of different linkers, as should be appreciated by those skilled in the art. While specific embodiments of the linking group Y are discussed in greater detail below, the present invention is not intended to be limited to any particular linking group.

As illustrated in FIGS. 1A and 1B, the linking group Y attaches to one of the carbon nodes available on the cyclobutane ring. The chelating agent X attaches to the linking group Y.

It is contemplated that the chelating agent X will be a strong chelating agent, the parameters of which should be understood by those skilled in the art. While a strong chelating agent is considered as a preferred embodiment of the present invention, it is contemplated that a weaker chelating agent may be employed under certain circumstances. As a result, the invention is intended to encompass chelating agents other than strong chelating agents.

The radioisotope Z attaches to or is associated with the chelating agent X. As depicted in FIGS. 1A and 1B, the radioisotope Z forms the terminus of the molecular segment that attaches, via the linking group Y to one of the carbon nodes in the cyclobutane ring. As should be appreciated by those skilled in the art, the radioisotope Z need not be exactly the last molecule in the molecular chain. Other variations are possible and are intended to fall within the scope of the invention.

Concerning the radioisotope Z, metallic radioisotopes encompass a preferred group of radioisotopes for the amino acid analog of the present invention. While metallic radioisotopes encompass a broad selection of potential metals in the periodic table, it is contemplated that certain non-metals also may be employed without departing from the scope of the present invention.

As should be appreciated by those skilled in the art, the amino acid analog molecule of the present invention may be in substantially pure syn-stereoisomeric or anti-stereoisomeric form, or in a mixture thereof. While this is preferred, it is also contemplated that other forms may be employed without departing from the scope of the present invention, as should be appreciated by those skilled in the art.

Figure 2A:
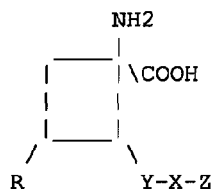
FIGS. 2A and 2B provide illustrations of two examples of the locations of additional moiety R groups that may be provided for the molecules depicted in FIGS. 1A-1B.
Figure 2B:
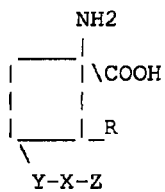

As shown in FIGS. 2A and 2B, the amino acid analog molecule of the present invention also may include an additional moiety R. The moiety R may be selected independently from a group that includes, but is not limited to, CH$_3$, C$_2$H$_5$, C$_3$H$_8$, C$_4$H$_{10}$, etc. It is also contemplated that isomeric forms of these moieties may be employed. In the contemplated embodiments of the amino acid analog of the present invention, the moiety R may be attached to one of the remaining two positions of the cyclobutane ring.

Figure 3:
FIG. 3 illustrates a chemical formula showing one contemplated example of the formation of a linker group.

As discussed above, those skilled in the art should recognize that the linking group Y may be selected from a wide variety of molecular compounds. In at least one contemplated embodiment, the linking group Y may be —NH-p-CHSN-Bn-. This represents the result of reaction of the isothiocyanate arm of the bi-functional chelator with amine as illustrated by the chemical equation depicted in FIG. 3.

In an alternative, contemplated embodiment, the linking group Y may be —NH—CO—, which is the result of a condensation reaction of an amine group (—NH2) with a carboxyl group (—COOH).

As noted, other linking groups Y may be employed. However the two examples described herein are contemplated to encompass the preferred linking groups Y.

The strong chelating agent X may be one of the following: (1) DCTA, (2) DOTA, (3) DTPA, (4) EDTA, (5) NOTA, (6) PCTA, (7) TETA, (8) TE2A, or (9) DO2A. While the precise details about these chelating agents should be known to those skilled in the art, a brief summary is provided below.

DCTA is an abbreviation for diaminocyclohexanetetraacetic acid, which has a reported chemical formula of $C_{14}H_{22}N_2O_8 \cdot H_2O$. The two-dimensional structure for this compound is set forth below.

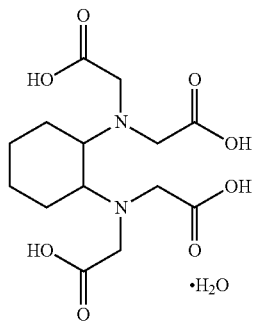

EDTA is short-hand for ethylenediaminetetraacetic acid, which has the formula $[CH_2N(CH_2CO_2H)_2]_2$. The two-dimensional chemical formula for this chelating agent is set forth below.

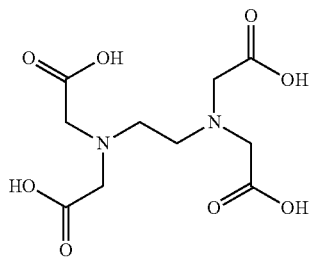

DOTA is also known as 1,4,7,10-tetraazacyclododecane-1,4,7,10-tetraacetic acid. The two-dimensional chemical formula for this chelating agent is expressed as follows:

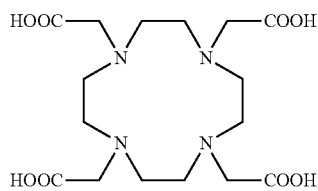

DTPA is also known as diethylene triamine pentaacetic acid and is another chelating agent. DTPA reportedly has the following two-dimensional chemical formula.

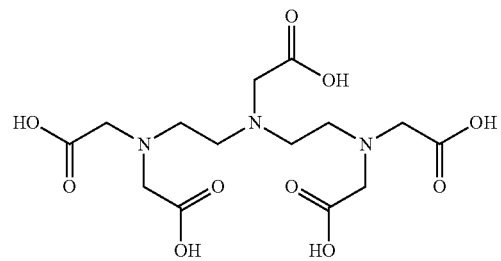

TETA is another chelating agent. TETA is also known as 1,4,8,11-tetraazacyclotetradecane-1,4,8,11-tetraacetic acid. TETA has a two-dimensional chemical formula is reportedly as follows:

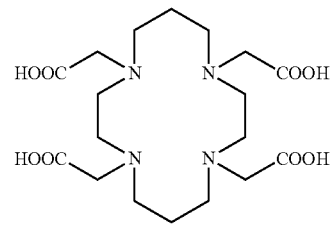

NOTA is still another chelating agent. NOTA is also known as 1,4,7-triazacyclononanetriacetic acid. NOTA has a reported two-dimensional formula as follows:

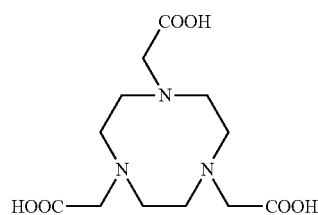

PCTA is still another chelating agent. PCTA is also known as 3,6,9,15-tetraazabicyclo [9.3.1]pentadeca-1(15),11,13-triene-3,5,9-triacetic acid. PCTA reportedly has the following two-dimensional structure.

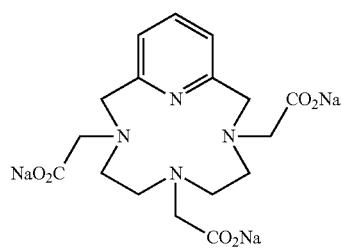

TE2A is another chelating agent, which is also known as 4,11-bis(carboxymethyl)-1,4,8,11-tetraazabicyclo [6.6.2]- hexadecane. TE2A reportedly has the following two-dimensional structure.

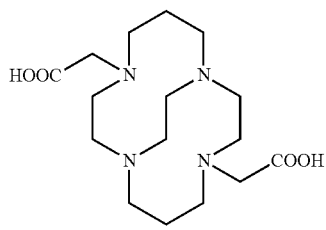

DO2A is still another chelating agent that is otherwise known as 4,10-bis(carboxymethyl)-1,4,7,10-tetraazabicyclo[5.5.2]tetradecane. The two-dimensional structure for DO2A is reportedly as follows:

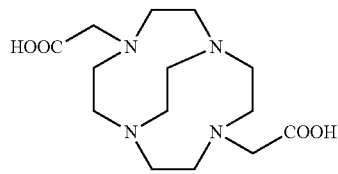

As should be apparent to those skilled in the art, there are numerous other chelating agents that may be employed without departing from the scope of the present invention. The chelating agents discussed above are considered to be exemplary of the invention.

The metal radioisotope Z may be one of the following: Cu-60, Cu-61, Cu-62, Cu-64, Cu-67, Ga-67, Ga-68, Y-86, Y-88, Y-90, Sr-85, Sr-89, Gd-153, Gd-157, Sm-153, Lu-177, W-185, Re-186, Re-188, or Ir-192. As should be apparent, for purposes of the present discussion, the atomic number of the radioisotope follows the elemental designation rather than preceding it (as may be done in some circumstances). The preparation of each of these isotopes should be known to those skilled in that art and, therefore, additional discussion is not provided here.

It is contemplated that the metal Z may be Ga-68 or Cu-62 provided from an automated microprocessor-controlled Ge/Ga or Zn/Cu generator and purification system, respectively, with an injectable radiopharmaceutical preparation step integrated into such a system. An injectable radiopharmaceutical preparation may be characterized, for example, as being prepared in a way that ensures that the resulting composition is: (a) sterile, (b) non-pyrogenic, and (c) has tightly controlled pH, purity and concentrations of all active and inert ingredients.

As discussed above, the radioisotopes of these metals Z are not anticipated to be produced by a cyclotron or require access to a cyclotron for production. As a result, these radioisotopes do not prohibit medical facilities from relying on radioisotope usage simply because they do not have a cyclotron available to them.

In many cases, it is contemplated that the half-lives of radioisotopes incorporated into the amino acid analogs of the present invention will that exceed those of cyclotron-produced radioisotopes.

One embodiment of the present invention employs a strong chelating agent with Cu-64 and/or Ga-68 isotopes. As should be appreciated by those skilled in the art, Ga-68 is available from a Ge/Ga generator. It is noted that cyclotron-produced Cu-64 is useful for pre-clinical studies in laboratory animals, while Ga-68 is useful for clinical applications.

While a strong chelating agent is contemplated for use with the present invention, it is also contemplated that other chelating agents may be employed without departing from the scope of the present invention. For example, a moderate chelating agent may be employed, as required or desired by the extant circumstances.

In one contemplated embodiment, the present invention also encompasses a diagnostic composition for tumor imaging that may be comprised of the radiolabeled compound, i.e., the amino acid analog of the present invention, prepared as described above. It is contemplated that the amino acid analog will include a pharmaceutically-acceptable carrier. A pharmaceutically-acceptable carrier encompasses one or more compounds that are combined with the amino acid analog so that the analog may be delivered to a suitable subject.

In one contemplated embodiment, a kit for production of a radiopharmaceutical is contemplated. The kit may include a septum closed vial, the design of which should be appreciated by those skilled in the art. In summary, a septum closed vial is a vial that includes at least two internal compartments separated by a septum, membrane, or other divider. One compartment of the septum closed vial is expected to contain a lyophilized or freeze-dried version of the amino acid analog, together with a suitable excipient (i.e., a bulking agent) and compounds providing pH adjustment to the range 5.0-7.8, and additionally providing adjustment to physiological isotonicity. In the other compartment, a small volume of sterile water may be provided so that, when the septum is broken, the water admixes with the remaining components to reconstitute the vial contents (i.e., bring the contents into solution) and create a solution that may be injected into a subject.

In another contemplated embodiment of the invention, tumor imaging by positron emission tomography or single photon emission tomography may be conducted using the amino acid analog as described above. The method includes: (a) administering to a subject (i.e., a human subject), known or suspected to have a tumor, the radiolabeled compound; (b) allowing sufficient time for desired compound to be biodistributed in the subject; and (c) measuring the distribution of the compound by means of PET or SPECT.

In an alternative embodiment, radiotherapy may be implemented by administering (in either one or multiple doses) the amino acid analog, as described above, to a tumor-bearing individual. While the invention is contemplated to be employed for tumor therapy, the amino acid analog may be employed for other treatments involving radioisotopes, as should be appreciated by those skilled in the art.

Figure 4:
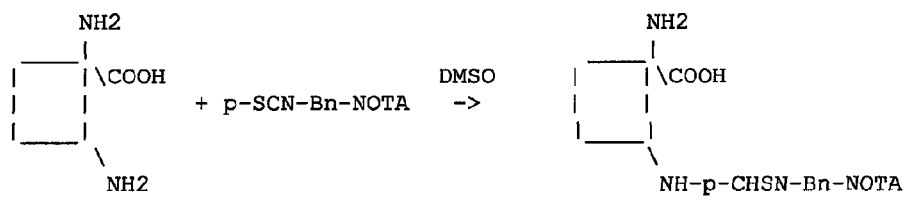
FIG. 4 provides an illustration of one example of the synthesis of an amino acid molecule.

In an alternative embodiment as illustrated in FIG. 4, a precursor compound with a second —NH2 moiety may be employed to synthesize the desired compound. In this embodiment, the precursor may be reacted with a bi-functional chelating agent such as p-SCN-Bn-DOTA or p-SCN-Bn-NOTA, with a subsequent step of HPLC-separation and purification of the reaction products. The bi-functional chelating agent may react effectively with the precursor in dimethyl sulfoxide media at room temperature.

In yet another embodiment, pairs of radioisotopes of the one chemical element can be utilized to react with the same amino acid of the present invention: one shorter-lived isotope like Ga-68 is used for the tumor imaging, whereas longer-lived Ga-67 can be used for radioisotope therapy. Such an approach ensures that, during radiotherapy, the biodistribution of the therapeutic drug will mirror the one observed at the diagnostic stage of tumor imaging.

Other embodiments are contemplated to fall within the scope of the present invention. The present invention is not intended to be limited solely to the embodiments described herein. To the contrary, those skilled in the art should appreciate equivalents and variations that also are intended to fall within the scope of the present invention.

What is claimed is:

1. An amino acid analog, in at least one of syn-stereoisomeric form, anti-stereoisomeric form, or a combination thereof, comprising:
   a cyclobutane ring with at least an amine group and a carboxyl group attached to one carbon node of the cyclobutane ring and a chain of moieties Y-X-Z attached to one of remaining three carbon nodes of the cyclobutane ring,
   wherein X is 1,4,7-triazacyclononane,
   wherein Y is —NH-p-CHSN-benzene,
   and
   wherein Z is a metal radioisotope selected from the group consisting of Cu-61, Cu-62, Cu-64, and Ga-68.

2. The amino acid analog of claim 1, further comprising at least one moiety R selected from the group consisting of of $CH_3$, $C_2H_5$, $C_3H_8$, and $C_4H_{10}$, wherein R is attached to one of the remaining two carbon nodes on the cyclobutane ring.

3. A diagnostic composition for tumor imaging comprising the amino acid analog of claim 1 and a carrier.

4. A kit for production of a radiopharmaceutical, comprising: a septum closed vial containing at least one of a lyophilized or freeze-dried amino acid analog according to claim 1; an excipient; at least one compound providing pH adjustment to the range 5.0-7.8 and additionally providing adjustment to physiological isotonicity for injection when admixed with a volume of sterile water, wherein the at least one compound reconstitutes the vial contents by bringing the vial contents into solution.

5. A method of tumor imaging by at least one of positron emission tomography (PET) or single photon emission tomography (SPECT), comprising: (a) administering to a subject, a tumor-revealing amount of the amino acid analog of claim 1; (b) allowing sufficient time for biodistribution in the subject; and (c) measuring distribution of the amino acid analog by means of PET or SPECT.

6. A method of tumor radiotherapy comprising administering an effective amount of the amino acid analog of claim 1 and a radioisotope to a subject having a tumor.

7. An amino acid analog, in at least one of syn-stereoisomeric form, anti-stereoisomeric form, or a combination thereof, comprising:
   cyclobutane ring of the formula

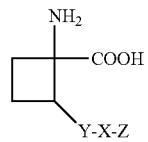

a)

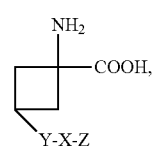

b)

wherein X is 1, 4, 7-triazacyclononane
wherein Y is —NH-p-CHSN-benzene, and
wherein Z is a metal radioisotope selected from the group consisting of Cu-61, Cu-62, Cu-64, and Ga-68.

8. The amino acid analog of claim 7 further comprising at least one moiety R selected wherein the cyclobutane ring has the formula

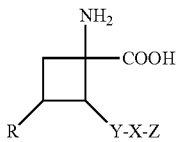

a)

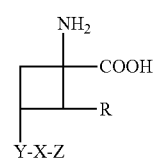

b)

and R is selected from the group consisting of $CH_3$, $C_2H_5$, $C_3H_8$, or $C_4H_{10}$.

* * * * *